(12) United States Patent
Leadlay et al.

(10) Patent No.: US 7,018,808 B2
(45) Date of Patent: Mar. 28, 2006

(54) POLYKETIDES AND THEIR SYNTHESIS AND USE

(75) Inventors: Peter Francis Leadlay, Cambridge (GB); James Staunton, Cambridge (GB); Lake Ee Khaw, Cambridge (GB)

(73) Assignee: Biotica Technology Limited, Cambridge (GB)

( * ) Notice: Subject to any disclaimer, the term of this patent is extended or adjusted under 35 U.S.C. 154(b) by 495 days.

(21) Appl. No.: 10/307,595

(22) Filed: Dec. 2, 2002

(65) Prior Publication Data

US 2003/0104585 A1    Jun. 5, 2003

Related U.S. Application Data

(63) Continuation of application No. 09/424,751, filed as application No. PCT/GB98/01559 on May 28, 1998, now abandoned.

(30) Foreign Application Priority Data

May 28, 1997  (GB) ................................... 9710962

(51) Int. Cl.
  *C12P 1/00*  (2006.01)
  *C12P 17/00* (2006.01)
(52) U.S. Cl. .................... 435/41; 435/75; 435/117; 435/183; 435/252.35; 536/23.2
(58) Field of Classification Search .................... None
  See application file for complete search history.

(56) References Cited

FOREIGN PATENT DOCUMENTS

| EP | 0589703 | 3/1994 |
|---|---|---|
| WO | WO 9410843 | 5/1994 |

OTHER PUBLICATIONS

McDaniel, et al., "Engineered Biosynthesis of Novel Polyketides", Science, 262:1546-1550, (1993).
C. D. Denoya et al., "A Second Branched-Chain α-Keto Acid Dehydrogenase Gene Cluster (*bkdFGH*) from *Streptomyces avermitilis*: Its Relationship to Averxmectin Biosynthesis and the Construction of a *bkdF* Mutant Suitable fox the Production of Novel Antiparasitic Avermectins", Journal of Bacteriology, 77(12) : 3504-3511 (1995).
E. Hafner et al., "Branched-Chain Fatty Acid Requirement for Avermectin Production by a Mutant of *Streptomyces avermitilis* Lacking Branched-Chain 2-Oxo Acid Dehydrogenase Activity", The Journal of Antibiotics, 44(3) : 349-356 (1991).
Li Tang et al., "Amino Acid Catabolism and Antibiotic Synthesis: Valine is a Source of Precursors for Macrolide Biosynthesis in *Streptomyces ambofaciens* and *Streptomyces fradiec*", Journal of Bacteriology, 176(19) : 6107-6119 (1994).
C. J. Dutton et al., "Novel Avermectins Produced by Mutational Biosynthesis", 44(3) : 357-365 (1991).
N. Lomovskaya et al., "Gene disruption and replacement in the rapamycin-producing *Streptomyces hygroscopicus* strain ATCC 29253", Microbiology, 143: 875-883 (1997).
I. Molnar et al., "Organisation of the biosynthetic gene cluster for rapamycin in *Streptomyces hygroscopicus*: analysis of genes flanking the polyketide synthase", Gene, 169: 1-7 (1996).
T. Schwecke et al. "The biosynthetic gene cluster for the polyketide immunosuppressant repamycin", Proc. Natl. Acad. Sci. USA, 92: 7839-7843 (1995).
L. L. Khaw et al., "Mutational Biosynthesis of Novel Rapamycins by a Strain of *Streptomyces hygroscopicus* NRRL 5491 Disrupted in rapL, Encoding a Putative Lysine Cyclodeaminase", Journal of Bacteriology, 180(4) : 809-814 (1998).

*Primary Examiner*—Nashaat T. Nashed
(74) *Attorney, Agent, or Firm*—Dann, Dorfman, Herrell & Skillman, P.C.

(57) ABSTRACT

The rapamycin gene cluster is an example of a gene cluster which includes a gene (rapL) leading to the formation of a precursor compound (pipecolic acid, in this case) which is required for inclusion in the larger product (rapamycin) produced by the enzymes encoded by the cluster. We have produced a mutant strain containing a rapamycin gene cluster in which the rapL gene is disabled. The strain does not naturally produce rapamycin but does so if fed with pipecolic acid. By feeding with alternative carboxylic acids we have produced variants of rapamycins. Tests have shown biological activity.

2 Claims, 4 Drawing Sheets

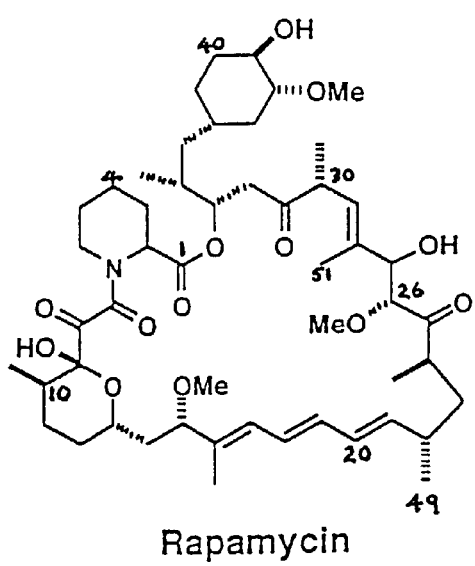
Rapamycin
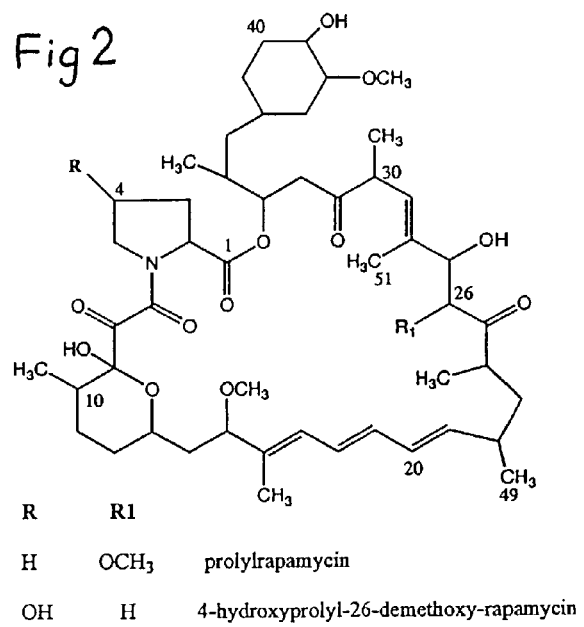
Fig 2
| R | R1 | |
|---|---|---|
| H | OCH₃ | prolylrapamycin |
| OH | H | 4-hydroxyprolyl-26-demethoxy-rapamycin |
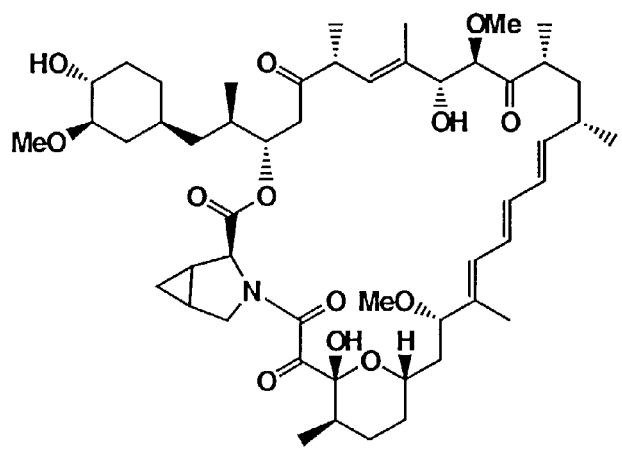
trans-3-aza-bicyclo(3.1.0)hexane-2-carboxylic acid rapamycin

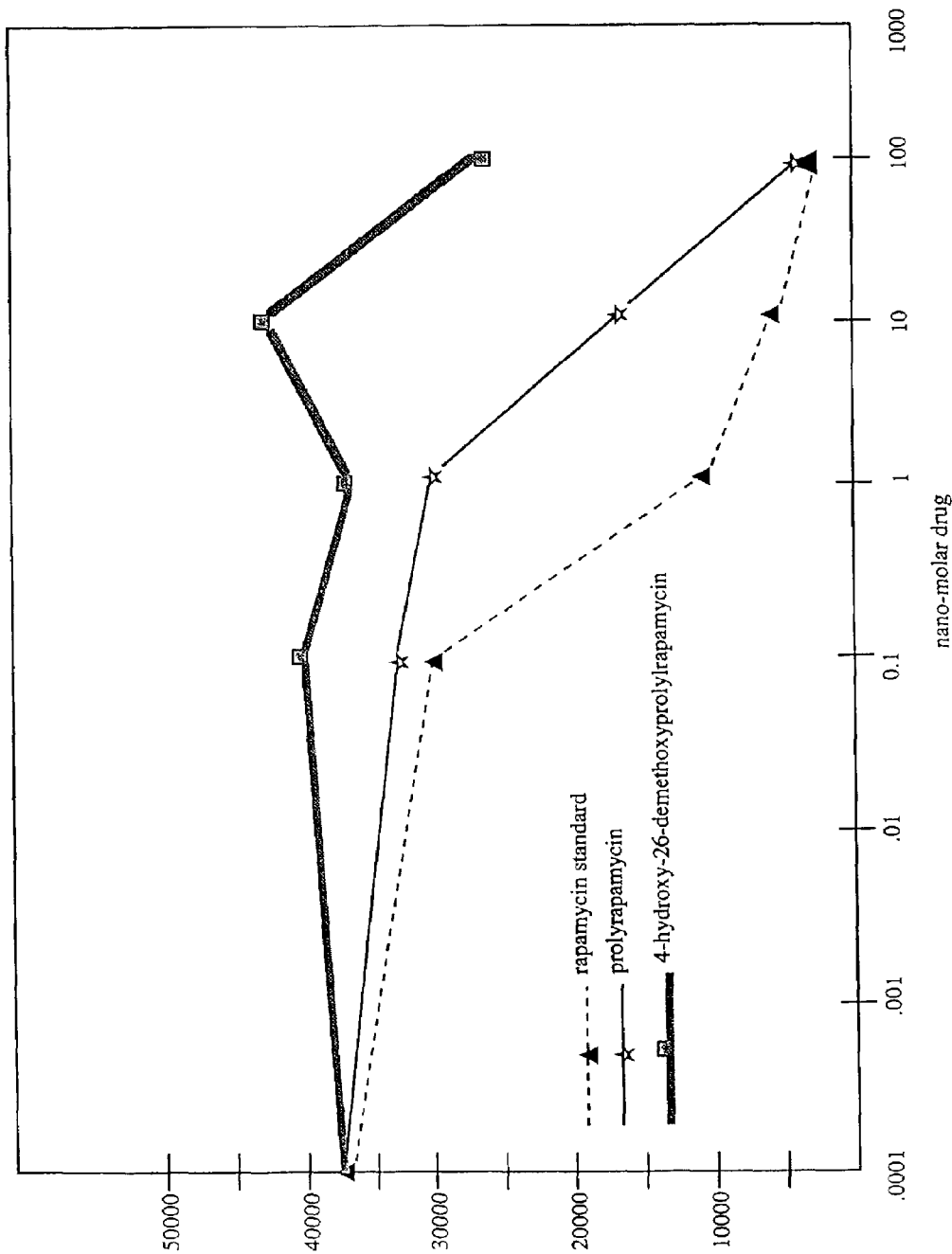
Fig. 4 DNA synthesis at 45 - 48h in 536 cells after 48h rapalogue therapy

POLYKETIDES AND THEIR SYNTHESIS AND USE

This application is a continuation of U.S. patent application No. 09/424,751, filed Nov. 29, 1999, now abandoned which is the U.S. National Phase Application of PCT/GB98/01559, filed May 28, 1998. The entire disclosure of U.S. patent application No. 09/424,751 is incorporated by reference herein.

The present invention relates to polyketides and their synthesis and use. It is particularly, but not exclusively, concerned with variants of rapamycin.

Rapamycin (see FIG. 2) is a lipophilic macrolide, of molecular weight 914, with a 1,2,3-tricarbonyl moiety linked to a pipecolic acid lactone. Sequencing of the putative biosynthetic genes of rapamycin has revealed the presence of three exceptionally large open reading frames encoding the modular polyketide synthase (Schwecke et al., *P.N.A.S.* 92 (17) 7839–7843 (1995)). On either side of these very large genes are ranged open reading frames which appear to encode enzymes that would be required for rapamycin biosynthesis.

The cluster also contains a novel gene (rapL) whose product is proposed to catalyse the formation of the rapamycin precursor L-pipecolate (2) through the cyclodeamination of L-lysine (1) (Molnar et al., *Gene* 169, 1–7 (1996)):

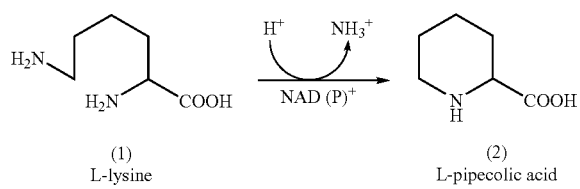

(1) L-lysine      (2) L-pipecolic acid

The biosynthesis of rapamycin requires a modular polyketide synthase, which uses a shikimate-derived starter unit and which carries out a total of fourteen successive cycles of polyketide chain elongation that resemble the steps in fatty acid biosynthesis. L-pipecolic acid is then incorporated into the chain, followed by closure of the macrocyclic ring, and both these steps are believed to be catalyzed by a pipecolate-incorporating enzyme (PIE), the product of the rapP gene. Further site-specific oxidations and O-methylation steps are then required to produce rapamycin.

We have now found that we can genetically engineer an *S.hygroscopicus* organism in which the (rapL) gene is inactivated. The organism cannot produce rapamycin under normal growth conditions but can do so if fed pipecolate. Furthermore feeding the mutant organism with different substrates leads to the production of variants of rapamycin. The same general method can be applied to other systems which involve a precursor compound which is produced by a gene product, e.g. the very closely related FK506 and immunomycin systems which also involve pipecolate.

Thus according to the present invention in a first aspect there is provided a process of modifying a gene cluster involved in the biosynthesis of a polyketide, said gene cluster including a gene ("the precursor gene") responsible for the production of an enzyme which is responsible for the production of a precursor compound which is incorporated into said polyketide; said process comprising the step of deleting or inactivating said precursor gene. Suitably said process of deleting or inactivating said precursor gene employs phage-mediated gene replacement. In preferred embodiments of the invention the gene cluster is the gene cluster for the production of rapamycin in *S.hygroscopicus* and the precursor gene is the rapL gene whose product is responsible for the production of L-pipecolate.

In a second aspect the invention provides a process for producing a polyketide comprising modifying a gene cluster by the process according to the first aspect and expressing the modified gene cluster in the presence of a variant precursor compound which is incorporated so that a variant polyketide is produced. For the rapamycin system, examples of the variant precursor compound include L-proline, L-trans-4-hydroxyproline, L-cis-4-hydroxyproline, L-cis-3-hydroxyproline and trans-3-aza-bicyclo[3,1,0]hexane-2-carboxylic acid.

In further aspects the invention provides polyketides as producible by the above method, pharmaceuticals comprising such polyketides, and the use of such polyketides in preparing pharmaceutical compositions, e.g. immunosuppressants containing rapamycin variants.

Some embodiments of the invention will now be described in greater detail with reference to the accompanying drawings in which;

FIG. 2 shows structures of rapamycin and some variants; and

FIGS. 3 and 4 illustrate the effects of rapamycin and variants on human lymphoblastoid cell lines.

Figure 1:
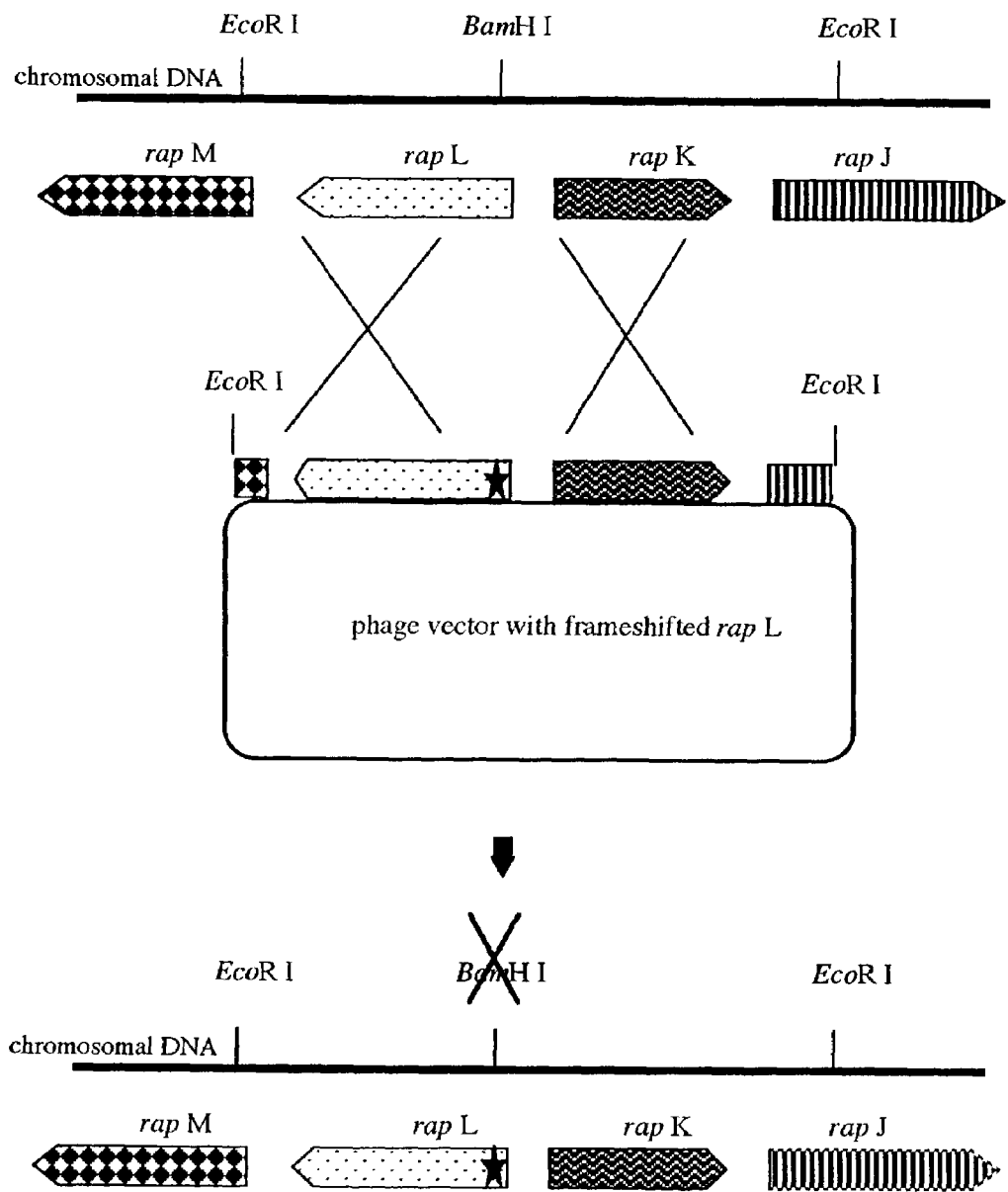
FIG. 1 shows a portion of the rapamycin gene cluster, wild type and mutated, and the phage vector used to perform mutation.

In order to facilitate the production of variant rapamycins, a chromosomal mutant of *S.hygroscopicus* was created by phage φC31-mediated gene replacement using the method of Lomovskaya et al. [Microbiology (UK) 1997, 143, 815–883]. A unique BamH I site was found 42 bp into the rapL gene (1032 bp long). This BamH I site was removed by end-filling with *E.coli* DNA polymerase I thus creating a frameshift in the rapL gene. A 3 kb EcoR I fragment encompassing the entire rapL gene flanked by rapK and part of the rapM genes respectively was cloned into the phase vector, KC515. The recombinant phage was used to transfect *S.hygroscopicus*. A double recombination event resulted in the creation of a chromosomal mutant of *S.hygroscopicus* with a frameshift in rapL. This is summarised in FIG. 1.

Materials and Methods

Note: the reader is also referred to L. E. Khaw et al., *J. Bacteriol.*, 180 (4) 809–814 (1998) which is incorporated herein by reference, for both experimental details and discussion of the work and the background thereto.

Materials. All molecular biology enzymes and reagents were from commercial sources. Viomycin was a gift from Pfizer, L-pipecolic acid, L-proline, 3,4-dehydroproline, picolinic acid, pyrrole-2-carboxylic acid, trans 4-hydroxyproline, cis 4-hydroxyproline, cis 3-hydroxyproline and (±)-trans-3-aza-bicyclo [3,1,0]hexane-2-carboxylic acid were obtained from Aldrich Chemical Company.

Bacterial Strains, Phases and Growth Conditions

*Escherichia coli* DH10B (GibcoBRL) was grown in 2×(tryptone-yeast extract) medium as described by Sambrook et al, ("*Molecular Cloning*", Cold Spring Harbor (1989)). Vector pUC18 was obtained from New England Biolabs. or Sigma Chemical Co. *E. coli* transformants were selected with 100 mg/ml ampicillin. The rapamycin producer *Streptomyces hygroscopicus* NRRL 5491 (from ATCC) and its derivatives were maintained on SY agar (Soluble starch 1.5%; yeast extract 0.1%; $K_2HPO_4$ 0.1%; $MgSO_4 \times 7 H_2O$ 0.1%; NaCl 0.3%; N-tri[Hydroxymethyl] methyl-2-aminoethanesulfonic acid (Tes) buffer 30 mM, pH7.4; agar 1.5%), and cultivated in Tryptic Soy Broth with 1.0% glucose, 100 mM MES pH6.0, supplemented with 10 ug/ml viomycin when required. *S.lividans* J11326 (D A Hopwood et al: "*Genetic Manipulation of Streptomyces: a laboratory manual*", The John Innes Foundation, Norwich, England (1985)) was cultivated in YEME (Hopwood et al., 1985) or Tap Water Medium (0.5% glucose; 1% sucrose; 0.5% tryptone; 0.25% yeast extract; 36 mg EDTA; pH 7.1). Liquid cultures were grown at 30° C. in Erlenmeyer flasks with shaking at 200–250 rpm. Infection with the atr actinophage KC515 (Hopwood (1985) op. cit. and K. F. Chater in: "*The Bacteria*"IX (119–158), New York 1986) and its derivative ΦΔrapL (present work) were done on solid DNA medium supplemented with 10 mM $MgSO_4$, 8 mM $Ca(NO_3)$ and 0.5% glucose (Hopwood et al., 1985).

Isolation and in Vitro Manipulation of DNA

DNA manipulations, PCR and electroporation procedures were carried out as described in Sambrook et al (1989). Total *S.hygroscopicus* DNA was isolated using the Gibco genomic DNA isolation kit. Southern hybridizations were carried out with probes labelled with digoxigenin using the DIG DNA labelling kit (Boehringer Mannheim). DNA fragments for labelling and subcloning were isolated with the Qiaex (Qiagen) gel extraction kit.

Construction of ΦΔrapL Carrying a Frameshift in the rapL Gene for Homologous Recombination in *S.hygroscopicus* pUC3EcoRI was constructed by cloning a 3034 bp Eco RI fragment (nucleotides 93956 to 96990 of the rap cluster) (T. Schwecke et al., *P.N.A.S.* 92, 7839–7843 (1995)) encompassing the entire rapL gene flanked by rapK and part of the rapM genes respectively into an Eco R1-cut pUC18 modified vector where the Bam HI site in the polylinker region has been removed. A unique Bam HI site (starting at nucleotide 95036 of the rap cluster) was found 42 bp into the rapL gene (nucleotide 95078 to 94047 of the rap cluster; 1032 bp long). Plasmid pUC3Eco RI was digested with Bam HI and the cohesive ends were filled in by treating it with *E.coli* DNA polymerase I (Klenow fragment). The ligated plasmid DNA was redigested with Bam HI and used to transform *E.coli*. Ampicillin resistant transformants were selected and their plasmid DNA checked for the removal of the Bam HI site by restriction enzyme analysis. This was confirmed by DNA sequencing. The 3 kb insert was excised from the plasmid with Eco RI and the cohesive ends blunt-ended by treatment with *E.coli* DNA polymerase I (Klenow fragment). The blunt-ended insert was cloned into Pvu II cut phage vector KC515, resulting in ΦΔrapL.

Protoplasts of *S.lividans* J11326 were transfected with the phage construct as described by Hopwood et al. (1985). Recombinant phage was identified using PCR analysis. Infection of *S.hygroscopicus* NRRL 5491 with ΦΔrapL was done according to Lomovskaya et al (*Microbiology*, 143, 875–883 (1997)) on DNA plates supplemented with glucose, $MgSO_4$ and $Ca(NO_3)$. Lysogens were selected by overlaying the plates with 50 μg ml$^{-1}$ (final concentration) viomycin 24 h post-infection. Strains that had undergone a second recombination event deleting the integrated phage were identified by selecting viomycin sensitive isolates after three rounds of non-selective growth and sporulation on SY plates. The insertion and subsequent loss of the phage were confirmed by genomic Southern hybridizations.

Precursor Feeding and Fermentation of *S.hygroscopicus* ΔRapL

Precursor feeding of *S.hygroscopicus* ΔRapL was performed routinely in 500 ml flasks containing 100 ml of Tryptic Soy Broth with 1.0% glucose, 100 mM MES pH6.0, supplemented with the appropriate pipecolic acid analogue, at a final concentration of 1 mg/ml. *S.hygroscopicus* ΔRapL was also cultivated in 2 l flasks containing 400 ml of chemically-defined media as described by Cheng et al (*Appl. Microbiol. Biotechnol.* 43, 1096–1098, (1995)). For large scale fermentation, 10 μl of spores of *S.hygroscopicus* ΔRapL was used to inoculate a 100 ml flask containing 30 ml of Tryptic Soy Broth medium. The flask was incubated on a rotary shaker (300 rpm) at 28° C. for 4 days. 4 ml of the first seed culture was transferred to a 2 l flask (second seed culture) containing 400 ml of the medium and incubated on a rotary shaker (300 rpm) at 28° C. for 4 days. The second seed culture was transferred to a 20 l fermenter containing 15 l of the medium. Trans 4-hydroxyproline was added to the medium aseptically to a final concentration of 1 mg/ml. The fermentation was carried out at 28° C. for 4 days, with an agitation rate of 500 rpm. The cells were harvested and extracted with twice their volume of methanol overnight.

Purification and Analysis of Rapamycin and its Derivatives

After 3–4 days fermentation mycelia were collected by filtration and extracted with two volumes of methanol at room temperature for 1 h. The crude extracts were analysed by 1 lc-ms using a Finnigan MAT (San Jose, Calif.) LCQ with a Hewlett-Packard 1100 HPLC. The large scale fermentation was worked up similarly. The crude extract was evaporated to dryness and then purified by flash chromatography (Merck silica gel 60, no. 9385) with acetone/hexane 1/1. The fractions containing rapamycins were further purified by preparative HPLC on a 250×20 mm RP18 column (HPLC Technology, Macclesfield, UK) using standard conditions. The 15 l fermentation yielded about 15 mg of pure prolyl-rapamycin and 3 mg of 4-hydroxy-prolyl-26-demethoxy-rapamycin. NMR spectra were determined on a Bruker DRX 500 spectrometer.

Biological Activity of Rapamycin Analogues

Rapamycin induces a specific cell cycle arrest in G1 in the cell line 536, which is a human B lymphocytic line immortalised by Epstein Barr virus infection. The potency of each analogue was compared to that of rapamycin using the 536 cells as a bioassay. The 536 cells (obtained from the human genetic mutant cell repository, Camden, N.J., USA) were cultured in Iscoves medium supplemented with 10% fetal calf serum. For bioassay, 536 cells were seeded into 96 well microtitre plates at 10,000 per well in 100 μl of growth medium. Drug stocks of 1 mM in DMSO were prepared and further dilutions were made to give a constant final concentration of 0.1% DMSO in growth medium. Control cultures were treated with 0.1% DMSO in growth medium; experimental cultures received a final concentration of $10^{-7}$M, $10^{-8}$M, $10^{-9}$M or $10^{-10}$M rapamycin or rapamycin analogue. Each culture was set up in triplicate and replicate plates were labelled with 1 μCi tritiated thymidine (Amersham International, specific activity 70 Ci/mM) per well for 3 h at either 0 h; 24 h; or 48 h incubation with drugs. At the respective time points the cultures were harvested onto glass fibre paper to trap the DNA following water lysis; free nucleotides were washed away. Radioactivity incorporated into the filter discs/trapped DNA was counted in a Packard scintillation counter using biodegradable scintillation fluid.

Results

Characterisation of a Frameshift Chromosomal Mutation in the RapL Gene

To confirm that the rapL gene product is indeed involved in the biosynthesis of rapamycin as a precursor feeder, the frameshift chromosomal mutant *S.hygroscopicus* ΔRapL was isolated as described in Materials and Methods. This mutation was investigated by Southern blot hybridization using the 3 kb EcoRI fragment (93956–96990) to probe Bgl II/Bam HI digested chromosomal DNA. Analysis of the wild-type *S.hygroscopicus* shows the expected 5.9 kb (representing nucleotides 89118–95036) and 2.7 kb Bam HI/Bgl II fragments (representing nucleotides 95036–97710) after hybridisation. When chromosomal DNA of *S.hygroscopicus* ΔRapL was treated similarly, only a 8.6 kb Bam HI/Bgl II fragment (representing nucleotides 89118–97710) was detected, indicating that the Bam HI site at position 95036 has been removed. This was confirmed by PCR analysis. Chromosomal DNA was subjected to PCR using oligonucleotide primers identical to, respectively, the sequences from nucleotide 93950 to 93968; and from 96990 to 97010. The expected 3 kb DNA fragment was amplified from wild type DNA and, following BamIII digest, two bands roughly 2 kb and 1 kb in size were detected. In samples containing *S.hygroscopicus* ΔRapL chromosomal DNA the 3 kb PCR product amplified was found to be resistant to BamHI digestion.

Precursor Feeding of the Chromosomal Mutant *S.hygroscopicus* ΔRapL

Growing cultures of the mutant *S.hygroscopicus* ΔRapL were fed with different amino acid precursors (table 1). Only the three proline derivatives were found to be incorporated as judged by LC-MS. The main rapamycin derivative in the fermentations apart from prolyl rapamycin is a compound with m/z 908 which could correspond to a hydroxy-rapamycin lacking a methoxy group. Smaller amounts of a compound with m/z 938 were also detected which would correspond to hydroxy-prolyl-rapamycin. MS-fragmentation experiments as well as the characteristic UV spectra clearly indicated that these compounds are rapamycin derivatives with a hydroxyproline incorporated. In order to get enough material for NMR characterisation we fed hydroxyproline on a large scale to the mutant (15 L broth) and isolated 3 mg of the compound with m/z 908 as described in material and methods. The NMR data (table 2) showed the chemical shifts and couplings expected for the hydroxy-proline spin system. The changed chemical shifts for the positions 26 and 27 and the unchanged shifts for positions 38–40 as compared to rapamycin proved that the methoxy group is missing at position 26. MS-fragmentation data (table 3) confirmed these findings. This can be inferred from the loss of the C15–C26-fragment leading to a fragment with m/z 644 for both of the new rapamycin derivatives. Furthermore, the loss of the C28–C42-fragment (322 amu) can be seen for both compounds as well as for rapamycin, indicating that there is no modification in this part of the molecules. The ions at m/z 807 and 777 respectively which are equivalent to the loss of the amino acid (131 amu) confirm the presence of OH-proline. This means that the compound with m/z 938 is 4-hydroxyprolyl-rapamycin.

TABLE 1

| Compound fed | Incorporation | Mass (m/z. M + Na⁻) | Retention time LC-MS (min) | Main Product |
|---|---|---|---|---|
| L-pipecolic acid | Yes | 936 | 8.84 | rapamycin |
| L-proline | Yes | 922 | 7.99 | prolyl-rapamycin |
| L-trans-4-hydroxyproline | Yes | 938/908 | 5.35/6.29 | 4-hydroxyprolyl-rapamycin and 4-hydroxyprolyl-26-demethoxyrapamycin |
| L-cis-4-hydroxyproline | Yes | 938/908 | 5.35/6.29 | as above |
| L-cis-3-hydroxyproline | Yes | 938/908 | 5.35/6.29 | 3-hydroxyprolyl-rapamycin and 3-hydroxyprolyl-26-demethoxyrapamycin |
| picolinic acid | No | | | |
| pyrrole-2-carboxylic acid | No | | | |

TABLE 2

| Position | $^1$H8 (ppm) | $^{13}$C8 (ppm) |
|---|---|---|
| 1 | | 171.30 |
| 2 | 5.24 | 58.17 |
| 3 | 2.65, 1.69 | 38.48 |
| 4 | 4.38 | 70.63 |
| 5 | 3.37, 2.94 | 56.53 |
| 26 | 3.58 | not determined |
| 27 | 3.89 | 70.63 |
| 38 | 2.93 | 83.90 |
| 39 | 3.37 | 73.95 |
| 40 | 1.99, 1.33 | 31.22 |
| 49 | 3.12 | 55.68 |
| 51 | 3.39 | 56.50 |

TABLE 3

| Rapamycin m/z | 4-hydroxyprolylrapamycin m/z | 4-hydroxyprolyl-26-demethoxyrapamycin m/z |
|---|---|---|
| 936 | 938 | 908 |
| 904 | 906 | 876 |
| 807 (loss of pipecolate, 129 amu) | 807 (los of hydroxyproline, 131 amu) | 777 (loss of hydroxyproline, 131 amu) |
| 642 | 644 | 644 |
| 614 | 616 | 586 |
| 596 | 598 | 568 |
| 582 | 584 | 554 |
| 564 | 566 | 536 |

Preparation of Trans-3-aza-bicyclo[3.1.0]hexane-2-carboxylic Acid Rapamycin

A 2 L fermentation of *S.hygroscopicus* ΔRapL fed with (+/−)-trans-3-aza-bicyclo[3.1.0]hexane-2-carboxylic acid (0.5 mg ml$^{-1}$) was grown for 5 days in TSBGM medium (Khaw et al., (1998) *J. Bacteriol.* 180, 809–814.). The cells were collected by filtration and extracted with 1 L of methanol at 4° C. overnight. High pressure liquid chromatograph-electrospray ionization mass spectrometry (HPLC-ESIMS) analysis of the crude methanol extract was performed at this stage using a Hewlett-Packard 1100 LC attached to a Finnigan-Mat LCQ mass spectrometer. Trans-3-aza-bicyclo[3.1.0]hexane-2-carboxylic acid rapamycin was detected in the fermentation broth.

The methanol extracts were combined and concentrated under reduced pressure. The aqueous residue was diluted with 500 mL of distilled water, and extracted three times with 500 mL of distilled ethyl acetate. The combined ethyl acetate extracts were dried with anhydrous sodium sulphate, and evaporated to dryness. The resulting yellow residue was purified by flash column chromatography on a 150 mm×30 mm (diameter) silica gel column [Merck 60] eluted isocratically with a 1:1 (v/v) mixture of acetone/hexane.

The fractions were analysed by electrospray mass spectrometry. MS—MS and Ms" were used to determine the structure of the new rapamycin in the fractions from the flash silica column.

The fractions containing trans-3-aza-bicyclo[3.1.0]hexane-2-carboxylic acid rapamycin were further purified by reversed-phase preparative HPLC on a 250×20 mm (diameter) Prodigy ODS3 column (Phenomenex) using gradient elution starting at 70/30 (v/v) acetonitrile/water rising linearly to 100% acetonitrile over 25 minutes. The 2 L fermentation yielded about 4 mg of pure trans-3-aza-bicyclo[3.1.0]hexane-2-carboxylic acid rapamycin.

High resolution MS of trans-3-aza-bicyclo[3.1.0]hexane-2-carboxylic acid rapamycin on a Bruker BioApex FTICR mass spectrometer using electrospray ionisation gave a sodiated molecular ion at m/z 934.52776, which confirmed the molecular formula to be $C_{51}H_{77}NO_{13}$.

Biological Activity

Figure 3:
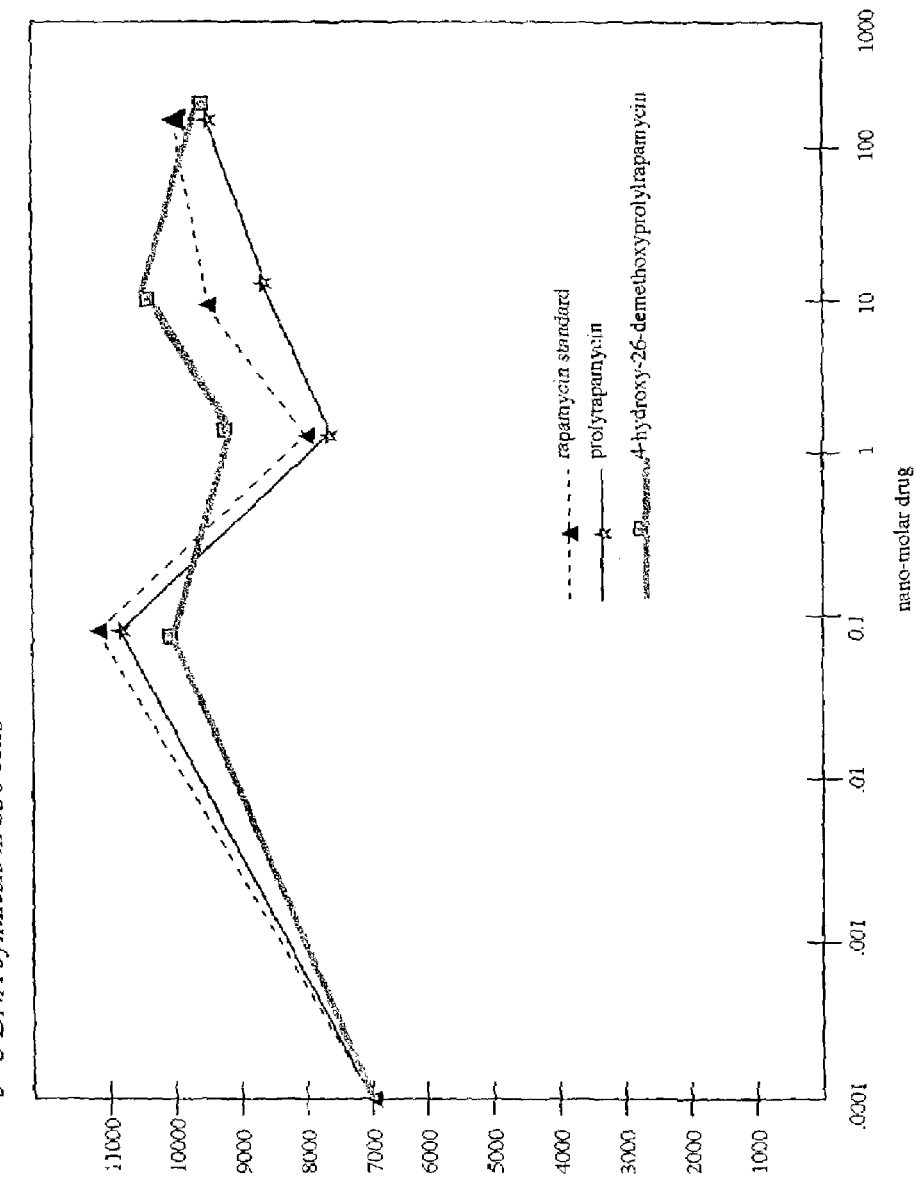

The dose response of human lymphoblastoid cell lines 536 was measured. In the experiment shown in FIG. 3 the mean cpm of radiolabelled thymidine incorporated into the untreated controls shows that 0–3 h drug exposure had no appreciable effect on DNA synthesis up to 100 nM of rapamycin, prolylrapamycin, or 4-hydroxy-prolyl-26-demethoxy-rapamycin. This implies that none of the compounds were toxic to the 536 cell line. After 24 and 48 hours (FIG. 4) the 536 cells showed a concentration-dependent inhibition of DNA synthesis with an ID50% of 1 nM for rapamycin; and 3 nM for prolylrapamycin. 4-hydroxy-prolyl-26-demethoxy-rapamycin was also inhibitory but did not reach 50% at 100 nM. Previous experiments have shown that rapamycin is a profound inhibitor of G1 progression in the 536 cell line (Metcalfe et al., *Oncogene* 15, 1635–1642 (1997)). This is also suggested in these experiments for the rapamycin analogues, since no significant effect was found at 3 h but inhibition was observed once the cell population had time to proceed through a complete cell cycle (24 h) and reach the drug arrest point.

The invention claimed is:

1. A process for producing an analogue of rapamycin in which an L-pipecolate moiety is substituted by a moiety derived from a precursor compound selected from the group consisting of L-proline, L-trans-4-hydroxyproline, L-cis-4-hydroxyproline, L-cis-3-hydroxyproline and trans-3-aza-bicyclohexane-2-carboxylic acid, said process comprising:
   a) a step of modifying the gene cluster for the production of rapamycin in a host microorganism, wherein said microorganism is *S. hygroscopicus*, said gene cluster including a gene, said gene being the rap L gene which encodes the enzyme which is responsible for the production of L-pipecolate which is incorporated into rapamycin, said step comprising the step of deleting or inactivating said rap L gene; and
   b) a step of culturing said host microorganism in the presence of said precursor compound to effect synthesis of said analogue of raparnycin, whereby said precursor compound is incorporated in said synthesis and said rapamycin analogue is produced.

2. A process according to claim 1, wherein said process of deleting or inactivating said precursor gene employs phage-mediated gene replacement.

* * * * *